United States Patent [19]

Jacobson

[11] 4,325,874

[45] Apr. 20, 1982

[54] PROCESS FOR PRODUCING ALKYLENE CARBONATES

[75] Inventor: Stephen E. Jacobson, Morristown, N.J.

[73] Assignee: The Halcon SD Group, Inc., New York, N.Y.

[21] Appl. No.: 267,152

[22] Filed: May 26, 1981

[51] Int. Cl.$^3$ .................. C07D 317/38; C07D 317/36
[52] U.S. Cl. .................................................. 260/340.2
[58] Field of Search ...................................... 260/340.2

[56] References Cited

U.S. PATENT DOCUMENTS

| | | | |
|---|---|---|---|
| 1,907,891 | 5/1933 | Steimmig et al. | 260/340.2 |
| 2,667,497 | 1/1954 | Cline | 260/340.2 |
| 2,773,881 | 12/1956 | Dunn | 260/340.2 |
| 2,784,201 | 3/1957 | Chitwood | 260/340.2 |
| 2,851,469 | 9/1958 | Testard | 260/348.16 |
| 3,025,305 | 3/1962 | Verdol | 260/340.2 |
| 3,884,984 | 5/1974 | Hirose et al. | 260/634 |
| 3,923,842 | 12/1975 | Wu | 260/340.2 |
| 4,009,183 | 2/1977 | Fumagalli et al. | 260/340.2 |
| 4,069,234 | 1/1978 | Wu | 260/340.2 |
| 4,160,116 | 7/1979 | Mieno et al. | 568/867 |
| 4,192,814 | 3/1980 | Johnson | 260/429 R |
| 4,224,223 | 9/1980 | Wheaton et al. | 260/340.2 |
| 4,226,778 | 10/1980 | Venturello et al. | 260/340.2 |
| 4,231,937 | 11/1980 | Kao et al. | 260/340.2 |
| 4,233,221 | 11/1980 | Raines et al. | 260/340.2 |
| 4,247,465 | 1/1981 | Kao et al. | 260/340.2 |

FOREIGN PATENT DOCUMENTS 2049662A 12/1980 United Kingdom .

Primary Examiner—Norma S. Milestone
Attorney, Agent, or Firm—William C. Long; Riggs T. Stewart; Harold N. Wells

[57] ABSTRACT

A process for the preparation of alkylene carbonates, particularly ethylene carbonate, by the reaction of the corresponding olefins with carbon dioxide in the presence of iodine or an iodide compound and an oxide or a weak acid salt of thallium (III). The thallium is reduced to the Tl(I) form which may be oxidized back to the Tl(III) form for reuse. Gold(III) oxide is also effective.

16 Claims, No Drawings

/ 1

PROCESS FOR PRODUCING ALKYLENE CARBONATES

PRIOR ART

This invention relates generally to a process for production of alkylene carbonates, especially to the production of ethylene carbonate by combining ethylene and carbon dioxide.

The prior art discloses methods for the production and use of alkylene carbonates, particularly, ethylene and propylene carbonates. These materials are useful for a number of purposes, and particularly as solvents. Ethylene carbonate also may be used as a precursor for ethylene oxide. Since ethylene carbonate is a solid under ambient conditions, it is more easily transported than ethylene oxide and can serve as a ready source of this material. For example, see U.S. Pat. No. 2,851,469, which discloses the use of polyhalogenated hydrocarbons as catalysts for the decomposition of ethylene carbonate. U.S. Pat. No. 4,069,234 also discloses the conversion of carbonate esters to vicinal epoxides.

Also, alkylene carbonates are considered intermediate compounds in recent disclosures of processes for producing alkylene glycols. British Publication GB Pat. No. 2,049,662 A discloses the use of molybdenum and/or tungsten catalysts in the reaction of alkylene carbonates with water. In U.S. Pat. No. 4,160,116 a process for production of alkylene glycols involves the reaction of the corresponding alkyl oxides with carbon dioxide and water in the presence of a suitable catalyst. It is believed that the reaction proceeds by the formation of the corresponding carbonate as an intermediate compound, which is then hydrated to form the glycol.

Alkyl carbonates have been made by at least three distinct approaches. First, they have been made by reacting the corresponding alkylene oxide and carbon dioxide. An example of the reaction is U.S. Pat. No. 2,667,497 which uses a catalyst of magnesium or calcium halides. In U.S. Pat. No. 2,773,881 alkyl amines serve as the catalyst. In the more recent patent, U.S. Pat. No. 4,233,221, anion exchange resins are used.

A second technique is the reaction of $CO_2$ with halohydrins. In U.S. Pat. No. 1,907,891 alkali carbonates are reacted with vicinal glycol chlorohydrins to produce the corresponding alkylene carbonates. In U.S. Pat. No. 2,784,201 the chlorohydrin is reacted with an alkali metal lower alkyl carbonate. In U.S. Pat. No. 3,923,842, as part of a three step process to produce an alkylene oxide, the second step is the reaction of a halohydrin with $CO_2$ to form an alkylene carbonate.

Two recent U.S. Pat. Nos. 4,226,778 and 4,231,937 also disclose the reaction of halohydrins with $CO_2$. In the first mentioned patent, bicarbonate of quaternary-onium compounds are reacted with a halohydrin. In the second mentioned patent, an alkylene iodohydrin is reacted with $CO_2$ in the presence of oxygen and catalyzed by a metal iodide and a metal carbonate.

The third approach is related more directly to the present invention since the alkyl carbonates are produced from the reaction of olefins with carbon dioxide. In U.S. Pat. No. 3,025,305 this reaction is carried out in the presence of two catalysts—the first a compound of a heavy metal oxide and the second a halide or hydroxy form of a ammonium compound. The conversions disclosed appear quite low.

In U.S. Pat. No. 4,009,183 the reaction is carried out in the presence of elemental iodine or an iodide compound and a manganese compound or other proposed oxygen carrying materials, including nitrogen oxides, nitrates, nitrites, and cobalt complexes.

In U.S. Pat. No. 4,224,223 the reaction is catalyzed by iodine or a compound thereof, along with an iron and/or copper compound on a support. A related disclosure is found in U.S. Pat. No. 4,247,465.

In the patents discussed above which relate to the reaction of olefins and carbon dioxide, no examples are given to the reaction of ethylene, which as will be seen has been found more difficult to react with carbon dioxide than the higher olefins.

Also of interest is U.S. Pat. No. 3,884,984 wherein halohydrins, specifically chloro- or bromohydrins, are shown to be made by reacting olefins, particularly ethylene, with water and chlorine or bromine ions in the presence of a thallium (III) salt of a strong acid which is reduced to thallium (I) and then reoxidized by the redox metal ions which are included. An atomic ratio of chlorine or bromine ions to thallium of at least 6:1 is shown to be needed to produce the halohydrin in large yields in preference to competing products. An acid pH of less than 4 is used. The presence of fluorine or iodine is stated to be detrimental.

Oxidation of thallous compounds to the thallic form has been disclosed in various publications. A number of these are discussed in U.S. Pat. No. 4,192,814.

It is of interest to provide further improvements in processes for the formation of alkylene carbonates, and particularly ethylene carbonate, by the reaction of olefins and carbon dioxide. Such an improved process is disclosed hereinafter.

SUMMARY OF THE INVENTION

A process for preparing alkylene carbonate comprises reacting the corresponding olefins with carbon dioxide in the presence of suitable amounts of iodine or an iodide compound and an oxide or a weak acid salt of thallium (III).

In a specific embodiment, ethylene is reacted with carbon dioxide to form ethylene carbonate using thallium (III). The reaction is carried out in the liquid phase at pressures in the range of about 8–70 kg/cm² absolute, typically 36–57 kg/cm² absolute and temperatures in the range of about 60°–120° C., typically 80°–100° C. The pH is preferably in the range of 4–8, preferably 5–7. Water may be used as a solvent, along with at least 1 wt% of a polar solvent soluble in water, particularly sulfolane, dioxane, t-butanol, tetrahydrofuran, and acetonitrile. The molar ratio of thallium (III) to iodine should be at least 1:1.

The iodine is preferably supplied as iodides of the Group Ia, Ib, IIa, IIb and VIII metals, in particular as the iodide of one or more of Na, K, Cu, Mg, Ca, Sr, Ba, Zn and Co.

Thallium having a valence of +3 is supplied as thallic oxide or a thallium (III) salt of a weak acid, such as the acetate or propionate.

Thallium (III) is reduced to thallium (I) during the formation of the alkylene carbonate. It may be reoxidized to Thallium (III) for reuse by contact with molecular oxygen under suitable conditions.

Gold (III) oxide also has been found to be effective.

DESCRIPTION OF THE PREFERRED EMBODIMENTS

The process of the invention is broadly applicable to the formation of alkylene carbonates having from 2-15 carbon atoms by the reaction of the corresponding olefin with carbon dioxide. The olefin may be generally described by the formula $R_1R_2C=CR_3R_4$, where $R_1$, $R_2$, $R_3$, and $R_4$ are hydrogen, alkyl, aryl, alkoxy, nitro or halo and $R_1$, $R_2$, $R_3$, and $R_4$ may be the same or different. The process is particularly useful for the preparation of ethylene carbonate by the reaction of ethylene and carbon dioxide, and for improving the rate of reaction of propylene with carbon dioxide to form propylene carbonate.

Although knowledge of the reactions by which ethylene carbonate is produced by the reaction of an olefin and carbon dioxide is not essential to practice the invention, it may be helpful to set forth an overall chemical reaction. The reaction of ethylene with carbon dioxide to form ethylene carbonate using thallic oxide is shown.

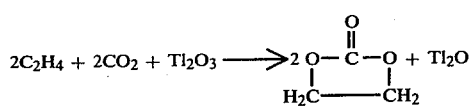

Since thallium is considered as a component in the reaction, the reduction of Tl(III) to Tl(I) is used in calculations as a measure of the potential formation of ethylene carbonate in the subsequent examples. Back-oxidation of thallium (I) to thallium (III) as discussed later may be employed to permit reuse of the thallium.

Although the olefins supplied to the reaction are preferably sufficiently pure to avoid unwanted by-products, nevertheless, minor amounts of impurities commonly found in olefins, such as alkanes may be tolerated.

Carbon dioxide ordinarily will be supplied in a gaseous form and preferably is of reasonable purity such as is found in commercially available carbon dioxide. Nevertheless, minor amounts of impurities such as carbon monoxide may be tolerated. Inert gases which do not affect the reaction may be present in any amount so long as the desired carbon dioxide partial pressure is provided. The reaction normally will be carried out at relatively high pressures with the reactants in the gas phase, particularly if ethylene carbonate is to be produced.

Suitable quantities of a thallium (III) compound and an iodine source will be disposed in a liquid medium suitable for this purpose. When water is the principal liquid, at least 1 wt% of an additional polar solvent soluble in water is needed. At the other extreme, the liquid medium could be a polar solvent containing at least about 1 wt% water. Examples of such solvents are sulfolane, dioxane, t-butanol, tetrahydrofuran, and acetonitrile. Acetonitrile has been found especially useful and is preferred. Other solvents which may be used alone or in combination with those already discussed, include dimethyl formamide, dimethyl sulfoxide, and hexamethyl phosphoramide. The amount of solvent relative to the amount of reacting materials is not critical, and the reacting materials may be either a homogeneous mixture or a heterogeneous mixture in the liquid medium.

While the presence of a thallium (III) compound has been found to be necessary, not all thallium (III) compounds are equally useful. Thallic oxide ($Tl_2O_3$) is particularly preferred. Alternatively, a thallium (III) salt of a weak acid, for example, an acetate, propionate, and butyrate may also be used. For purposes of this disclosure the term "weak acid salt" refers to a salt which under the conditions described will provide a pH of about 4-8. It has been found that thallium (III) salts of strong acids, such as thallic chloride and thallic nitrate, are substantially less effective. Since as will be seen, the thallium is reduced from the (III) valence to the (I) valence during the reaction, the use of thallium (I) compounds is ineffective, unless, of course, they are oxidized to the thallium (III) form. The molar ratio of thallium (III) to iodine to be used to carry out the reaction preferably should be about 1:1, but the amount of thallium (III) should be equal to or greater than the amount of iodine present.

A source of iodine has been found to be essential. Other halogens are substantially less effective. Iodine may be present in elemental form or as an iodide compound, preferably as a metal iodide of Groups Ia, Ib, IIa, IIb, and VIII. In particular, the iodides of sodium, potassium, copper, calcium, magnesium, barium, strontium, zinc and cobalt are preferred.

The reaction when carried out under the conditions specified above will provide a reaction solution having a pH within the range of 4-8, preferably 5-7. If the pH is substantially lower the amount of ethylene carbonate formed is substantially reduced. The reaction may be carried out at temperatures in the range of about 60°-120° C., preferably in the range of 80°-100° C. The pressures used will generally be in the range of 8-70 kg/cm² absolute, and preferably in the range of 36-57 kg/cm² absolute.

According to the equation, thallium is reduced from the +3 valence to the +1 valence, when the alkylene carbonate is formed. While iodine in some form is not shown, it will be seen to be essential if the reaction is to proceed. Both thallium and iodine have been found necessary.

While the disclosures of U.S. Pat. Nos. 4,009,183 and 4,224,223 indicate that their methods are effective for producing ethylene carbonate, the examples only show propylene or butylene carbonate being prepared. It has been found that ethylene carbonate cannot be prepared with a substantial yield by these prior art methods, as will be seen below. Substantial quantities of by-products such as halohydrins are also produced in these prior art examples. A more effective method was needed and is provided by the present invention.

EXAMPLE I

Comparative Examples

Method of U.S. Pat. No. 4,009,183

A 200 cc Parr Instrument Co. magnetically-stirred titanium bomb was charged with 15 gms of water, 20 gms of acetonitrile, 3.5 gms of $MnO_2$, and 4.2 gms of $I_2$. The vessel was closed, flushed with carbon dioxide, and pressured to 22.1 kg/cm² absolute with ethylene and then to 50.3 kg/cm² absolute with carbon dioxide. The bomb was maintained at 80° C. for 4 hours, at which time it was cooled to room temperature and depressured. The liquid contents were analyzed for the presence of ethylene glycol, 2-iodoethanol and ethylene carbonate by gas chromatography. The yield of ethylene carbonate is 7.8%, calculated as the moles of ethylene carbonate produced divided by the mols of manganese (IV) initially present and available to be reduced as part of the reaction.

The experiment was repeated using 2.8 gms of $MnO_2$ and 5 gms of NaI with the result that only a 2.5% yield of ethylene carbonate was obtained.

Method of U.S. Pat. No. 4,224,223

The above experiment was repeated except that 40 gms of water and 10 gms of sulfolane, along with 1.6 gms of a catalyst consisting of 2.4 g $FeI_2$ and 0.8 g $CuSO_4.4H_2O$ deposited on 20 g of silica (surface area 400 m²/gm), and 6 gms of KI were initially charged to the Parr bomb. The vessel was closed, flushed with carbon dioxide and pressured to 15.1 kg/cm² absolute with ethylene and then to 43.2 kg/cm² absolute with $CO_2$ and then to 50.3 kg/cm² absolute with oxygen. The vessel was maintained at 120° C. for 4 hours, after which is was cooled to room temperature and depressured. No ethylene carbonate was found.

It will be clear from the above results that the conversion of ethylene to ethylene carbonate by the prior art methods is poor and an improved process is desirable. However, when the same catalyst was used to repeat Example 6 of U.S. Pat. No. 4,224,223 with propylene, formation of propylene carbonate was observed.

EXAMPLE II

The experiments of Example I were repeated using thallium (III) oxide as follows. A 200 cc titanium bomb was charged with 35 gms of water and 10 gms of acetonitrile, along with 4.6 gms of $Tl_2O_3$ and 2.9 gms of $CaI_2$. The vessel was closed, flushed with carbon dioxide, and pressured to 8.1 kg/cm² absolute with ethylene and then to 43.2 kg/cm absolute with carbon dioxide. The vessel was held at 90° C. for 4 hours, when it was cooled to room temperature and depressured. The pH of the liquid was 7. A yield of 61.8% ethylene carbonate was measured, based on the amount of Tl(III) originally present and available for reduction to the Tl(I) form. Measurement of the total Tl by atomic absorption and the Tl(III) remaining after the reaction by iodometric titration showed (by difference) that 84.4% of the Tl(III) had been converted to Tl(I) and thus the theoretical yield of ethylene carbonate could have been 84.8%. The selectivity to ethylene carbonate then is 72.9%, calculated as the actual yield versus the theoretical yield.

EXAMPLE III

The experiment of Example II was repeated with other sources of iodine, with the results tabulated below. All the tests were carried out for 4 hour periods, and except where noted, with the ethylene and carbon dioxide pressures of Example II.

TABLE A

| Test No. | Temp °C. | $H_2O/CH_3CN$, gms/gms | $Tl_2O_3$, gms | Iodine Source, gms | Products Ethylene Carbonate Yield % | Sel. % | Iodohydrin Yield % |
|---|---|---|---|---|---|---|---|
| 1 | 90 | 35/10 | 4.6 | 2.8 $MgI_2$ | 44 | 57.5 | 1.6 |
| 2 | 80 | 35/10 | 4.6 | 3.0 $ZnI_2$ | 59.2 | 71.8 | 8.0 |
| 3 | 90 | 35/10 | 4.6 | 3.0 $ZnI_2$ | 58.3 | 72.2 | 9.0 |
| 4 | 80 | 40/05 | 4.6 | 3.2 $ZnI_2$ | 61.4 | 78.3 | 12.6 |
| 5 | 90 | 40/05 | 4.6 | 3.2 $ZnI_2$ | 59.3 | 73.8 | 9.6 |
| 6 | 80 | 35/10 | 4.6 | 1.5 NaI | 22.2 | N/A | 0 |
| 7 | 80 | 35/10 | 4.6 | 2.1 $I_2$ | 93[1] | 93[1] | 6.2 |
| 8[2] | 90 | 40/05 | 4.6 | 3.9 $BaI_2$ | 72.5 | N/A | 1.9 |
| 9[3] | 90 | 30/15 | 4.6 | 3.4 $CoI_2$ | 58 | N/A | 0 |

[1] This experiment used 22.1 kg/cm² absolute ethylene pressure and 50.3 kg/cm² total pressure.
[2] Pressured with carbon dioxide to 32 kg/cm² absolute.
[3] Pressured with carbon dioxide to 57 kg/cm² absolute.

The importance of thallium (III) is shown in the following example in which no thallium is used.

EXAMPLE IV

Comparative Example

The experiments of Examples II & III were repeated using the following conditions. The bomb was charged with 35 gms of $H_2O$, 10 gms of $CH_3CN$, and 2.6 gms of $I_2$. It was pressured to 8.1 kg/cm² absolute with ethylene and then to 50.2 kg/cm² absolute with carbon dioxide. The vessel was held at 100° C. for 4 hours, cooled to room temperature and depressured. Only iodohydrin was found (yield 25% based on the iodine atoms present), no ethylene carbonate was detected.

The results show that free iodine was not effective to react ethylene with carbon dioxide to form ethylene carbonate when thallium (III) was lacking.

The importance of thallium (III) is shown in the following example where a thallium (I) salt is used instead.

EXAMPLE V

Comparative Example

The general procedures of the previous examples were followed, with a Parr bomb being charged with 32 gms of water, 10 gms of acetonitrile, 4.7 gms of $Tl_2CO_3$, and 2.8 gms of $ZnI_2$, then pressured to 8.1 kg/cm² absolute with ethylene and to 43.2 kg/cm² absolute with carbon dioxide. After 4 hours at 90° C. the vessel was cooled to ambient and depressured. No ethylene carbonate or iodohydrin was detected.

EXAMPLE VI

Comparative Example

In another test, the conditions of Test 1 of Example III were repeated except that no $Tl_2O_3$ was used. No conversion to ethylene carbonate, or even to iodohydrin, was detected.

The importance of an iodide source is shown in the following example, in which none is included in the reaction mixture.

EXAMPLE VII

Comparative Example

In another test repeating the conditions of Test 1 of Example III, no $MgI_2$ was included. Upon analyzing the vessel contents, no ethylene carbonate or iodohydrin was detected.

It has been found that water alone is inadequate as a solvent for the desired reaction of ethylene with carbon dioxide to form ethylene carbonate, as will be seen from the following example.

EXAMPLE VIII

A bomb was charged with 45 gms of water, 4.6 gms of $Tl_2O_3$ and 2.8 gms of $MgI_2$. After pressuring to 8.1 kg/cm² absolute with ethylene and then to 36.2 kg/cm₂ absolute with carbon dioxide, the vessel was held at 90° C. for 8 hours before cooling to room temperature and depressuring. No ethylene carbonate or 2-iodoethanol was detected when the contents were analyzed. It is concluded that a solvent, such as the acetonitrile used in the earlier examples is needed to supplement the water used.

EXAMPLE IX

Each of two bombs was charged with 35 gms of water, 4.6 gms of $Tl_2O_3$ and 2.8 gm of $MgI_2$. One was charged also with 10 gms of sulfolane and the other with 10 gm of dioxane. After pressuring to 8.1 kg/cm² absolute with ethylene and then to 33.4 kg/cm² absolute with carbon dioxide, each vessel was held at 90° C. for 4 hours before cooling to room temperature and depressuring. The yield of ethylene carbonate was found to be 19 and 25.8 percent respectively. The pH was 8 in each vessel.

The process of the invention is also applicable to other alkylenes, as illustrated in the following example showing its application to propylene carbonate.

EXAMPLE X

A 200 cc Parr bomb is charged with propylene, water, acetonitrile, $Tl_2O_3$, and an iodine source in the manner previously described. After completion of a 4 hour reaction the following results were obtained.

TABLE B

| Test No. | $CO_2$ Pressure kg/cm²abs | Temp °C. | Propylene, gms | $H_2O$ gms | $CH_3CN$, gms | $Tl_2O_3$, gms | Iodine Source, gms | Yield % |
|---|---|---|---|---|---|---|---|---|
| 10 | 50.2 | 90 | 5 | 22 | 22 | 4.6 | 2.4 CuI | 29.5 |
| 11 | 50.2 | 90 | 4 | 35 | 10 | 4.6 | 1.3 $I_2$ | 41.9 |
| 12 | 46.7 | 80 | 4 | 35 | 10 | 4.6 | 2.1 $I_2$ | 98 |

Thallium (III) salts of weak acids may also be used as a source of thallium (III), as shown in the following example.

EXAMPLE XI

The conditions of Example III are followed generally. A Parr bomb is charged with 17 gm of water, 5 gms of acetonitrile, 4.1 gms of thallic acetate, and 1.7 gms of zinc iodide and then pressured to 8.1 kg/cm² absolute with ethylene and to 36.2 kg/cm² absolute with carbon dioxide. After reacting the mixture at 90° C. for 4 hours the vessel is cooled to room temperature and depressured. The yield of ethylene carbonate is 34.8% based on the amount of thallium (III) originally present.

Gold (III) has also been found to be effective to carry out the oxidation of alkylene carbonates, as will be seen in the following example.

EXAMPLE XII

Experiments were carried out in a similar manner to that previously described. A 200 cc Parr bomb was charged with water, acetonitrile, gold (III) oxide, and an iodine source. The vessel was purged and pressured to 8.1 kg/cm² absolute with ethylene and then to 37.6 kg/cm² absolute with carbon dioxide. After reacting the mixture at 90° C. for 4 hours, the following results were obtained.

TABLE C

| Test No. | $H_2O$ gms | $CH_3CN$ gms | $Au_2O_3$ gms | Iodine gms | Yield, % Iodohydrin | Yield, % Ethylene Carbonate |
|---|---|---|---|---|---|---|
| 13 | 9 | 2 | 1.1 | 0.7 $CaI_2$ | 8.6 | 54 |
| 14 | 9 | 2 | 1.1 | 0.8 $ZnI_2$ | 27.8 | 56 |

Oxidation of Thallium (I to III) and Reuse

As thallium (III) is reduced to thallium (I) during the reaction which produces alkylene carbonates, it becomes inactive and must be regenerated by oxidation back to the +3 valence if the thallium is to be reused. This is obviously an important aspect of any practical use of the reaction, unless thallium (I) has some convenient use so that it can be employed in forming alkylene carbonate only once. Generally, oxidation of thallium (I) to (III) is desired. It has been found that such an oxidation can be carried out by contact with molecular oxygen at suitable conditions, as will be exemplified below. The chemical formula of the thallium (III) compound(s) is uncertain since the oxidation is carried out on solids having undetermined composition remaining after alkylene carbonate has been separated. However, the presence of carbonates and bicarbonates has been detected and these are believed to contribute to the back oxidation of thallium (I) to (III). As will be seen, the thallium (III) is in a form which can be reused.

EXAMPLE XIII

After the preparation of ethylene carbonate is carried out as described above the liquid remaining is filtered through a sintered glass filter to recover the insoluble thallium (I) compounds and metal iodide salts remaining. The liquid portion principally comprises solvents and ethylene carbonate, along with any iodohydrin and other by-products. The solids are dried at about 100° C. in air and then placed in a porcelain tray and inserted into a 2.4 cm diameter glass tube for back-oxidation. The tube is heated in an oven at the desired temperature and oxygen (saturated with water at 80° C.) is passed over the solids for a period of time suitable to complete the oxidation. After cooling, the solids are removed and the amount of thallium (III) measured by iodometric titration and the total amount of thallium measured by atomic absorption. During the oxidation iodine sublimes and is recovered by use of a cold trap to condense iodine from the exiting steam of oxygen. Where it is desired to demonstrate the effectiveness of the recovered thallium (III) for preparation of ethylene carbonate, the oxidized solids are combined with the condensed iodine.

The following table summarizes results obtained in experiments carried out as generally described above.

TABLE C

| Test No. | Weight of Sample, gms | Iodine Source | Temp, °C. | Time, hrs | $O_2$ flow l/hr | Conv. Tl(I) to III, % |
|---|---|---|---|---|---|---|
| 15 | 3 | $MgI_2$ | 400 | 2 | 50 | 65 |
| 16 | 1.5 | $CoI_2$ | 300 | 2 | 50 | 100 |

As the table shows, substantial back-oxidation of the solids containing thallium (I) can be obtained under the conditions described. Since the method used in Example XII might not be convenient for practical applications another technique has been tested, as described in the following example.

EXAMPLE XIV

The solids remaining after the preparation of ethylene carbonate are filtered on a sintered glass filter, transferred to a solvent in a 200 cc titanium Parr bomb and treated with oxygen under pressure. The results are shown in the table below.

TABLE D

| Test No. | Solvent gms | Weight of Sample, gms | Iodine Source | Temp, °C. | Time, hrs | $O_2$ pres. kg/cm² abs | Conv. Tl(I) to III, % |
|---|---|---|---|---|---|---|---|
| 17 | 20 $H_2O$ | 6 | $CoI_2$ | 220 | 4 | 57.3 | 23 |
| 18 | 10 $H_2O$ | 2 | $MnI_2$ | 220 | 4 | 57.3 | 13.5 |

For practical applications of the process of the invention, the thallium (III) obtained by oxidation of thallium (I) should be reusable in the reaction of ethylene and carbon dioxide to form ethylene carbonate. It has been found that reoxidized thallium can be successfully reused, as shown in the following example.

EXAMPLE XV

The solids oxidized in Test 15 of Example XII were combined with solids from similar tests (not shown) and used to form ethylene carbonate in the manner described in the earlier examples. The reaction was carried out at 90° C. for 4 hours with an ethylene pressure of 8.1 kg/cm² absolute and a total pressure including carbon dioxide of 43.2 kg/cm² absolute. A 2.3 g sample of the solids was used, along with 1 gm of iodine in 17 gms of water and 5 gm acetonitrile. The yield of ethylene carbonate was 98%, showing the effectiveness of the back oxidized thallium in the reaction.

What is claimed is:

1. A process for preparing alkylene carbonates by reacting the corresponding olefins with carbon dioxide comprising contacting the said reactants with suitable amounts of iodine or an iodide compound and an oxide or a weak acid salt of thallium (III).

2. The process of claim 1 wherein said olefin is ethylene.

3. The process of claim 1 wherein said reaction is carried out at pressures in the range of about 8–70 kg/cm² absolute and temperatures in the range of about 60°–120° C.

4. The process of claim 3 wherein said pressure is in the range of about 36–57 kg/cm² absolute and said temperature is in the range of about 80°–100° C.

5. The process of claim 1 wherein the molar ratio of thallium (III) to iodine is at least 1:1.

6. The process of claim 1 wherein said iodine compound is at least one metal iodide from Group Ia, Ib, IIa, IIb, and VIII metals.

7. The process of claim 1 wherein the process is carried out at a pH in the range of about 4–8.

8. The process of claim 7 wherein said pH is in the range of about 5–7.

9. The process of claim 1 wherein the reaction is carried out in the presence of water and at least 1 wt% of a polar solvent soluble in water.

10. The process of claim 9 where said solvent is selected from the group consisting of sulfolane, dioxane, t-butanol, tetrahydrofuran, acetonitrile, dimethyl formamide, dimethyl sulfoxide, and hexamethyl-phosphoramide.

11. The process of claim 10 wherein said solvent is acetonitrile.

12. The process of claim 6 wherein the iodine compound is at least one member of the group consisting of Na, K, Cu, Mg, Ca, Ba, Sr, Zn and Co.

13. The process of claim 1 wherein said thallium (III) salt of a weak acid is selected from the group consisting of one acetate, propionate, and butyrate.

14. The process of claim 1 further comprising the step of oxidizing to thallium (III) the thallium (I) resulting from the preparing of alkylene carbonates with molecular oxygen and reusing the reoxidized thallium (III).

15. A process for preparing alkylene carbonates by reacting the corresponding olefins with carbon dioxide comprising contacting the said reactants with suitable amounts of iodine or iodine compounds and an oxide of gold (III).

16. The process of claim 15 wherein said olefin is ethylene.

* * * * *